(12) United States Patent
Dunst (10) Patent No.: US 7,608,040 B1
(45) Date of Patent: Oct. 27, 2009

(54) DEVICE TO AID IN PLACING TRACHEAL TUBES (75) Inventor: Mordecai Dunst, Duarte, CA (US)

(73) Assignee: City of Hope, Duarte, CA (US)

( * ) Notice: Subject to any disclaimer, the term of this patent is extended or adjusted under 35 U.S.C. 154(b) by 98 days.

(21) Appl. No.: 10/783,093

(22) Filed: Feb. 23, 2004

Related U.S. Application Data (60) Provisional application No. 60/448,881, filed on Feb. 24, 2003.

(51) Int. Cl.
*A61B 1/267* (2006.01)
(52) U.S. Cl. .................. 600/187; 600/104; 600/156; 600/185; 600/190; 600/194
(58) Field of Classification Search ............. 600/185, 600/187, 188, 190, 194, 201, 205, 210, 237
See application file for complete search history.

(56) References Cited

U.S. PATENT DOCUMENTS

| | | | | |
|---|---|---|---|---|
| 2,911,968 A | * | 11/1959 | Schueler et al. | 600/187 |
| 3,626,471 A | * | 12/1971 | Florin | 600/205 |
| 4,126,127 A | * | 11/1978 | May | 600/187 |
| 4,256,099 A | * | 3/1981 | Dryden | 128/200.26 |
| 4,481,947 A | | 11/1984 | Chester | |
| 4,790,327 A | | 12/1988 | Despotis | |
| 4,832,020 A | | 5/1989 | Augustine | |
| 4,905,669 A | * | 3/1990 | Bullard et al. | 600/104 |
| 4,941,872 A | * | 7/1990 | Felix et al. | 604/27 |
| 5,003,962 A | | 4/1991 | Choi | |
| 5,024,218 A | | 6/1991 | Ovassapian et al. | |
| 5,038,766 A | | 8/1991 | Parker | |
| 5,042,469 A | | 8/1991 | Augustine | |
| 5,174,283 A | * | 12/1992 | Parker | 128/200.26 |
| 5,203,320 A | * | 4/1993 | Augustine | 600/187 |
| 5,235,970 A | | 8/1993 | Augustine | |
| 5,339,805 A | | 8/1994 | Parker | |
| 5,390,661 A | | 2/1995 | Griffith et al. | |
| 5,431,152 A | | 7/1995 | Flam et al. | |
| 5,513,627 A | | 5/1996 | Flam | |
| 5,607,386 A | | 3/1997 | Flam | |
| 5,665,052 A | * | 9/1997 | Bullard | 600/194 |
| 5,740,791 A | | 4/1998 | Aves | |
| 5,743,254 A | | 4/1998 | Parker | |
| 5,776,053 A | | 7/1998 | Dragisic et al. | |
| 5,803,898 A | | 9/1998 | Bashour | |
| 5,896,858 A | | 4/1999 | Brain | |
| 5,937,859 A | | 8/1999 | Augustine et al. | |

(Continued)

*Primary Examiner*—Linda C Dvorak
*Assistant Examiner*—Matthew J Kasztejna
(74) *Attorney, Agent, or Firm*—Rothwell, Figg, Ernst & Manbeck, PC (57) ABSTRACT

A laryngoscope includes a blade assembly with a base that is coupled to a handle. Attached to the blade assembly are two hollow guide tubes that generally follow along the longitudinal axis of the blade assembly. The two tubes are oriented at different angles of attack for directing aspirating and/or oxygenating tubes into different regions of the patient's oral cavity. The handle has an ergonomic shape to conform to the user's hand, thereby facilitating the user's application of a downward force necessary to effect laryngeal suspension. A tube extension/retraction mechanism effects user-controlled powered movement of an aspiration/oxygenation tube into or out of the patient's oral cavity. A bayonette connection is provided for connecting the blade assembly to the handle.

21 Claims, 10 Drawing Sheets

U.S. PATENT DOCUMENTS

| | | |
|---|---|---|
| 6,070,581 A | 6/2000 | Augustine et al. |
| 6,079,409 A | 6/2000 | Brain |
| 6,146,402 A | 11/2000 | Munoz |
| 6,248,061 B1 * | 6/2001 | Cook, Jr. .................... 600/187 |
| 6,251,069 B1 | 6/2001 | Mentzelopoulos et al. |
| 6,257,236 B1 | 7/2001 | Dutkiewicz |
| 7,013,899 B2 * | 3/2006 | Alfery et al. ........... 128/207.18 |

* cited by examiner

DEVICE TO AID IN PLACING TRACHEAL TUBES

This application claims the benefit of U.S. Provisional Patent Application No. 60/448,881, filed on Feb. 24, 2003, the contents of which are incorporated herein by this reference.

BACKGROUND OF THE INVENTION

1. Field of the Invention

The present invention relates generally to tracheal intubation devices and, in particular, to a tracheal intubation device that allows single handed laryngeal suspension, secretion aspiration, oxygenation, and visualization.

2. Background and Related Art

Laryngoscopes are generally used during tracheal intubation procedures, both in surgical situations and in any emergency situation requiring access to a patient's mouth and throat. Laryngoscopes are used to suspend the oral cavity, Pharynx and associated structures open for insertion of, for example, endotracheal tubes, which may facilitate positive pressure ventilation for the patient's lungs.

Generally, a laryngoscope comprises a handle and a blade portion. Laryngoscopes are commonly constructed from either stainless steel or chrome-plated brass, but can also be made of hard plastic. The handle portion is cylindrical and will typically contain a power source, generally a battery, which powers a light bulb attached to the blade portion. The light bulb illuminates the inside of a patient's mouth and throat during endotracheal intubation. The blade portion is detachably secured to the handle portion and extends away from the handle curving downwardly with respect to the top of the handle. Other types of blades are straight, extending nearly perpendicularly from the handle. Additionally, the blade portion may include a side wall, sometimes called a tongue deflector, which assists in manipulating and moving the patient's tongue to the side of the patient's mouth to permit direct visualization of the larynx/vocal cords and placement of the endotracheal tube.

Representative laryngoscopes comprising a blade and handle design are described in U.S. Pat. No. 6,251,069 to Mentzelopoulos et al. and U.S. Pat. No. 5,776,053 to Dragisic et al. U.S. Pat. No. 5,203,320 to Augustine discloses a tracheal intubation guide with a curved, open tubular device through which flexible tubes and the like can be guided into the trachea of a patient.

When using a laryngoscope with a standard curved blade, the blade is placed into the anatomical region called the vallecula. This is the space immediately anterior to the epiglottis at the base of the tongue. Optimally, pressure is exerted on the tongue by the operator at this location in an upward fashion to suspend the larynx and aid in visualization of the glottic aperture. It is through this glottic aperture that tracheal intubation is performed. Often times the glottic aperture is rendered difficult to visualize by secretions (i.e., blood, mucus, gastric contents, foreign debris, etc.).

Currently, the state of the art is for the operator to use one hand to suspend the larynx while the other hand has to periodically aspirate retained and unwanted secretions to visualize the glottis to allow for intubation of the trachea. Many times these secretions continue to build up after the operator has cleared them initially, thereby rendering the glottis poorly visualized once again. There are many occasions where secretions are so massive that continued aspiration of them is the only way to maintain an open glottic aperture. This situation requires the operator to use both hands simultaneously—one for suspension and one for aspiration—preventing early tracheal intubation.

In respiratory emergencies where time is of extreme importance (measured in seconds not minutes), single handed simultaneous suspension and aspiration would enable the opposite free hand to be ready to pass the tracheal tube past the glottic aperture.

None of these devices, however, provide dedicated means to allow for aspiration of secretions or for improved visualization, while simultaneously allowing for single-handed insertion of endotracheal tubes. There continues to exist a need for a tracheal intubation device that addresses all of these shortcomings.

SUMMARY OF THE INVENTION

The present invention is embodied in a number of aspects which may be employed independently, in combination, or in partial combinations.

According to one aspect of the invention, a blade assembly for a laryngoscope including a handle includes base for coupling to the handle, an elongated blade secured to the base, the elongated blade having a proximal end, a distal end, an upper surface, and a lower surface, a first guide tube secured to the upper surface of the elongated blade and having a proximal end and a distal end, and a second guide tube secured to the upper surface of the elongated blade adjacent the first guide tube and having a proximal end and a distal end, the first and second guide tubes being constructed and arranged to direct tubes extended therethrough into the oral cavity of a patient.

According to a further aspect of the invention, a handle for a laryngoscope, which includes a blade connected to an end of the handle for effecting laryngeal suspension, comprises ergonomic features for conforming to the hand of a user grasping the handle.

According to a further aspect of the invention, a laryngoscope comprises a handle to be grasped by a hand of a user, a blade connected to one end of the handle and extending generally transverse to the handle, a tube extension/retraction mechanism carried on the laryngoscope and constructed and arranged to effect powered extension or retraction of a tube along the blade into or from the oral cavity of a patient, and a trigger located on the handle for providing finger actuated control of the tube extension/retraction mechanism.

According to a further aspect of the invention, the laryngoscope includes a bayonet or "Twist To Lock" connection for releasably connecting the blade assembly to the handle.

In addition to the benefits of single-handed laryngeal suspension, secretion aspiration, oxygenation, and direct visualization, the apparatus of the present invention allows a fibre-optic cable to be easily inserted into the trachea, which can be connected to a video device for purposes of indirect visualization. Such indirect visualization is useful for documentation, instruction, or to assist in tracheal intubation.

With these and other objects, advantages, and features of the invention that will become hereinafter apparent, the nature of the invention may be more clearly understood by reference to the following detailed description of the invention and the appended claims.

DETAILED DESCRIPTION OF THE PREFERRED EMBODIMENTS

An exemplary embodiment of a device to aid in placing tracheal tubes according to the present invention is described herein.

Figure 1:
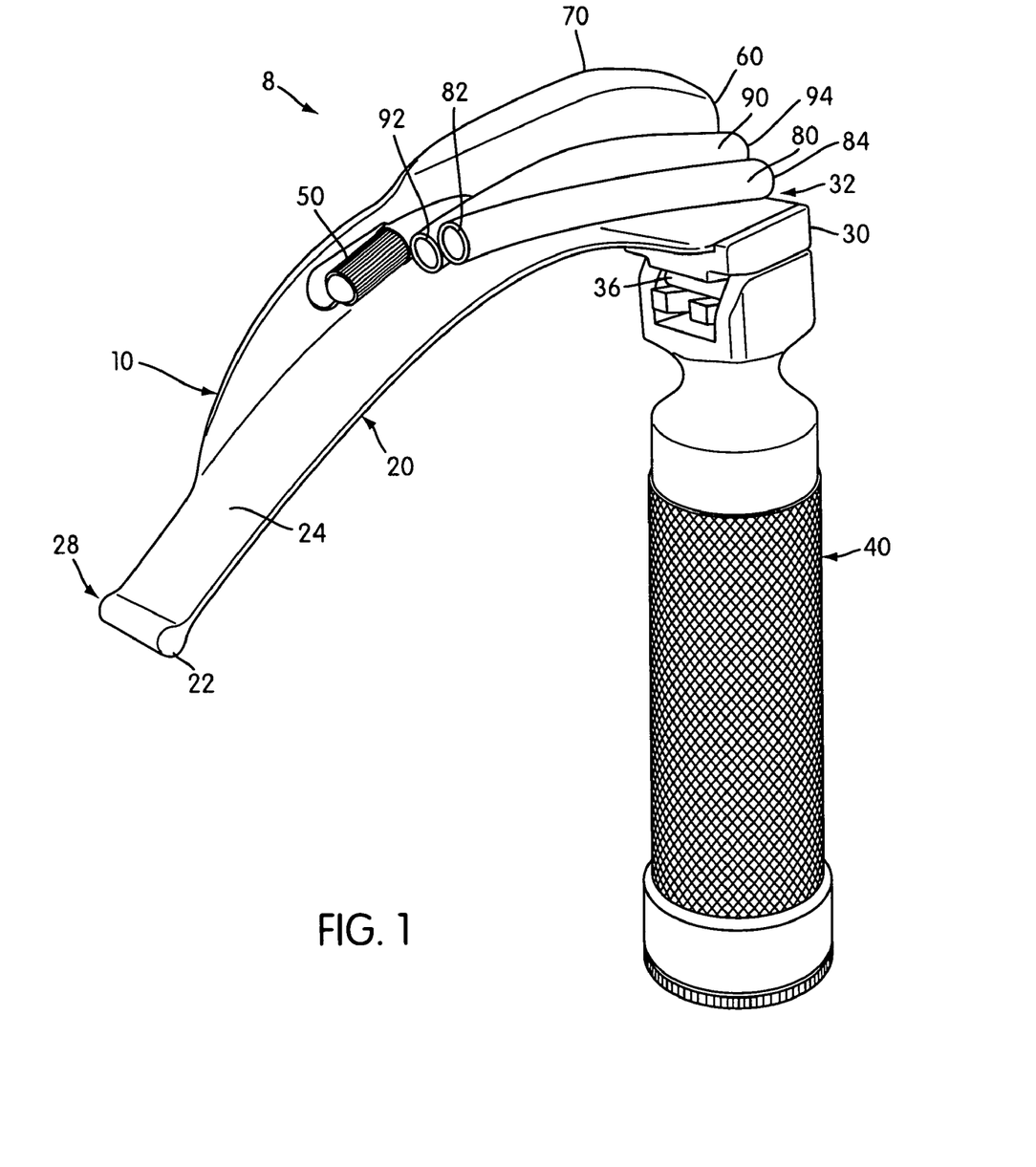
FIG. 1 is a perspective view of a laryngoscope including a blade assembly according to one aspect of the present invention.

Referring now in detail to the drawings there is in FIG. 1 a laryngoscope 8 including the blade assembly 10 according to one aspect of the present invention attached in a conventional manner to a handle 40. The blade assembly 10 comprises an elongated, curved blade 20, a base 30 for coupling blade assembly 10 to handle 40, a light source 50, a tongue deflector 60, a horizontal flange 70 attached to tongue deflector 60, a first guide tube 80, and a second guide tube 90.

Figure 2:
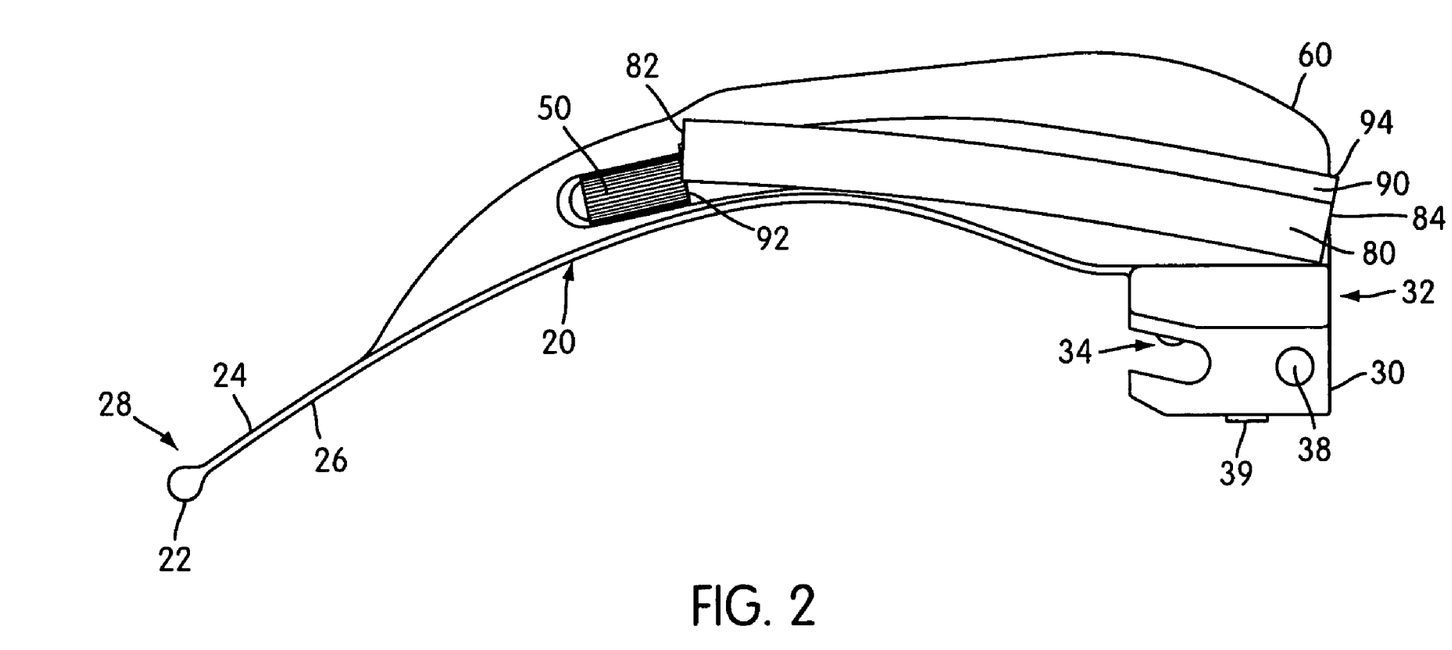
FIG. 2 is a right-hand side elevation of the blade assembly.
Figure 3:
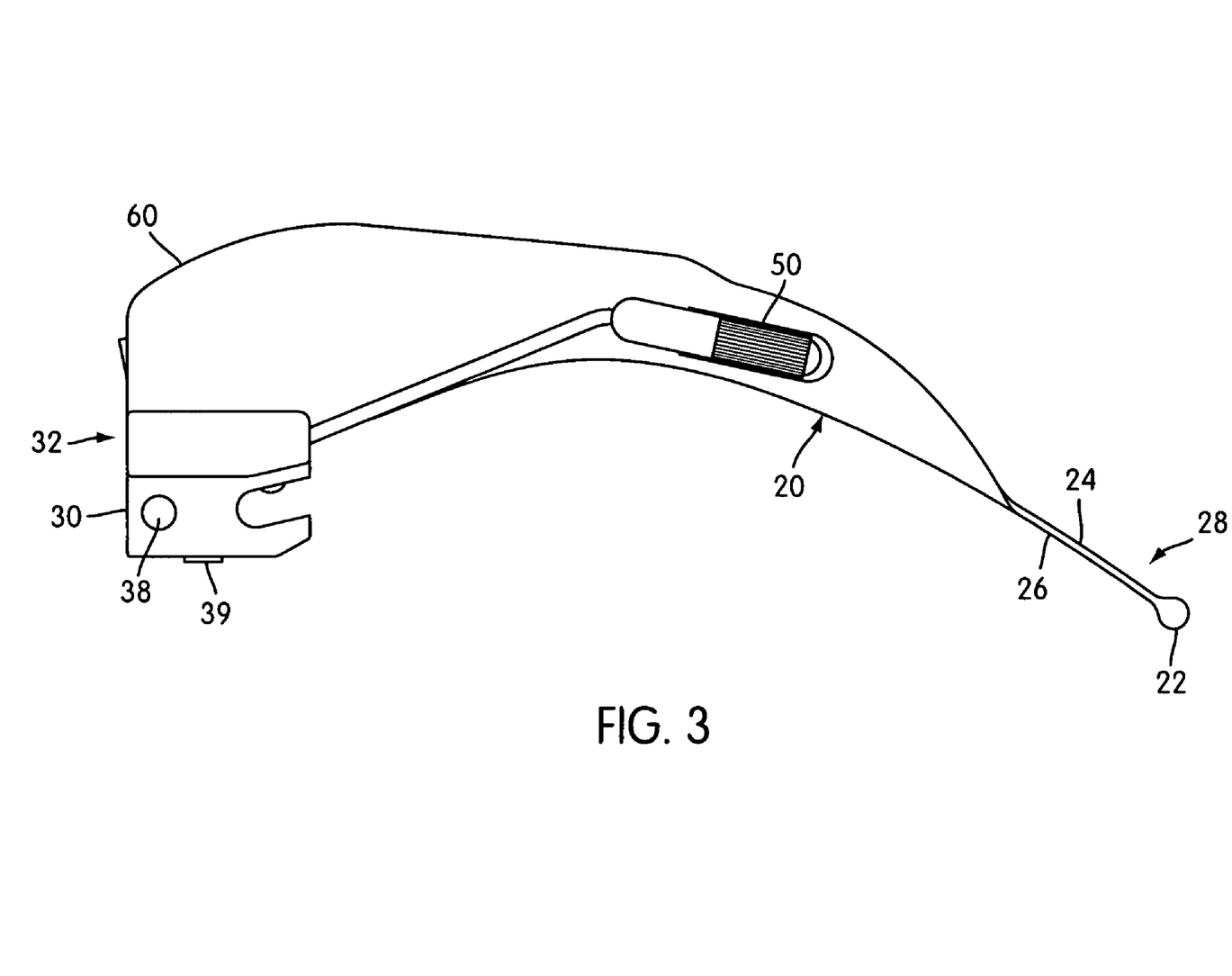
FIG. 3 is a left-hand side elevation of the blade assembly.
Figure 4:
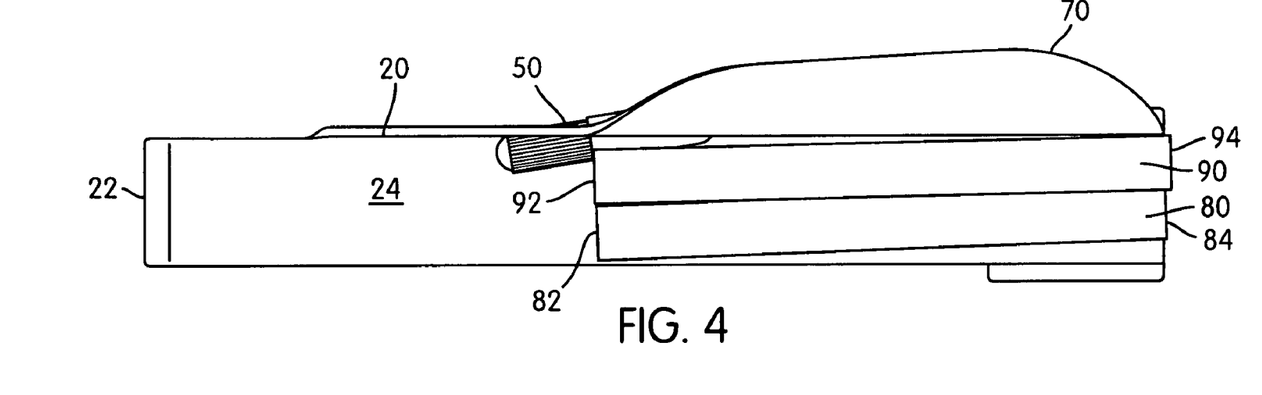
FIG. 4 is a top view of the blade assembly.

Viewing the curved blade 20 in more detail, there is in FIGS. 2-4 a proximal end 32, a distal end 28, an upper surface 24, and a lower surface 26. The distal end 28 incorporates a bulbous tip 22 projecting outward from the proximal end, which minimizes the risk of damage to tissues within the oral cavity when the laryngoscope is inserted into the patient's mouth. The curved blade 20 and handle 40 can be of any standard design wherein blades of different sizes, curvatures, and/or proportions accommodating the physical peculiarities of different patients may be interchangeably locked into a standard handle. A laryngoscope including a stainless steel handle and Macintosh blade by American Medical Supplies & Equipment would be a representative example.

As discussed, blade assembly 10 comprises a base 30 for mounting the blade assembly onto handle 40. The base includes a notched opening 34, and the handle includes a bar 36. To connect the blade assembly to the base, notched opening 34 is forcibly snapped into the bar on the handle by aligning the notched opening with the bar and pushing on the proximal end of the blade assembly. When correctly aligned, the blade assembly 10 will pivot around bar 36. To prepare the laryngoscope 8 for use on a patient, blade assembly 10 is rotated to a position in which the base 30 is seated atop the handle 40. When the blade assembly 10 reaches the proper position, spring-biased plunger ball bearings 38 on base 30 engage detents (not shown) on the handle to securely hold the blade assembly in proper position. Additionally, as blade assembly 10 is rotated into position, switch 39 contacts a switch on the handle (not shown), completing an electrical circuit and illuminating light source 50.

A first guide tube 80 and second guide tube 90, preferably thin-tube stainless steel, are attached to the blade 20 and generally follow along the longitudinal axis of elongated blade 20 on its upper surface 24, extending to approximately the midpoint of the elongated blade. First guide tube 80 has a distal end 82 and a proximal end 84, and second guide tube 90 has a distal end 92 and a proximal end 94.

Figure 5:
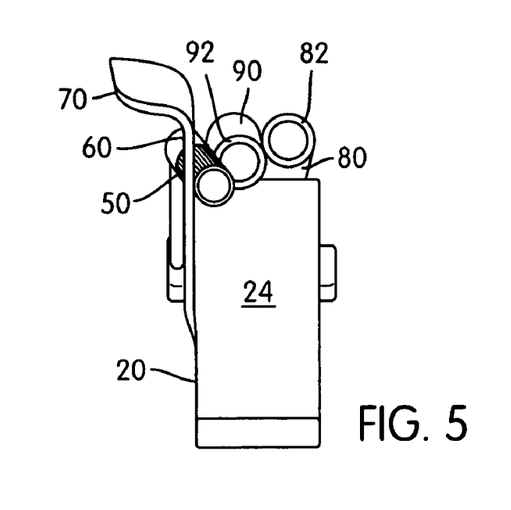
FIG. 5 is a distal end view of the blade assembly.
Figure 6:
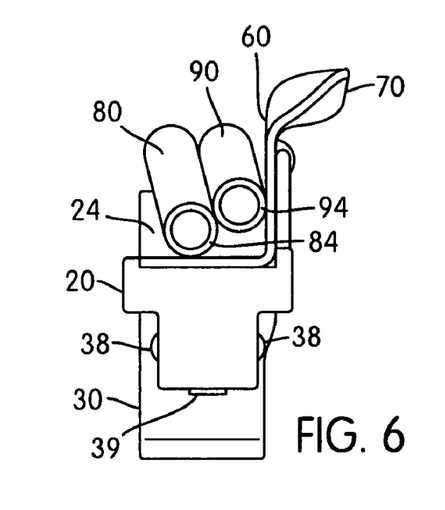
FIG. 6 is a proximal end view of the blade assembly.

First guide tube 80 is generally straight, and second guide tube 90 is curved in general conformity to the curvature of the blade 20. As illustrated in FIG. 5, the center of the distal end 82 of first guide tube 80 is disposed above the center of the distal end 92 of second guide tube 90 relative to the upper surface 24 of elongated blade 20. In the embodiments shown, as illustrated in FIG. 6, the center of the proximal end 84 of first guide tube 80 is disposed below the center of the proximal end 94 of second guide tube 90 relative to the upper surface 24 of elongated blade 20.

First guide tube 80 and second guide tube 90 can be securably fastened to the upper surface 24 of elongated blade 20 by any suitable bonding process, to include medical grade adhesive and welding. Alternatively, the tubes could be integrally formed with elongated blade 20.

Figure 7:
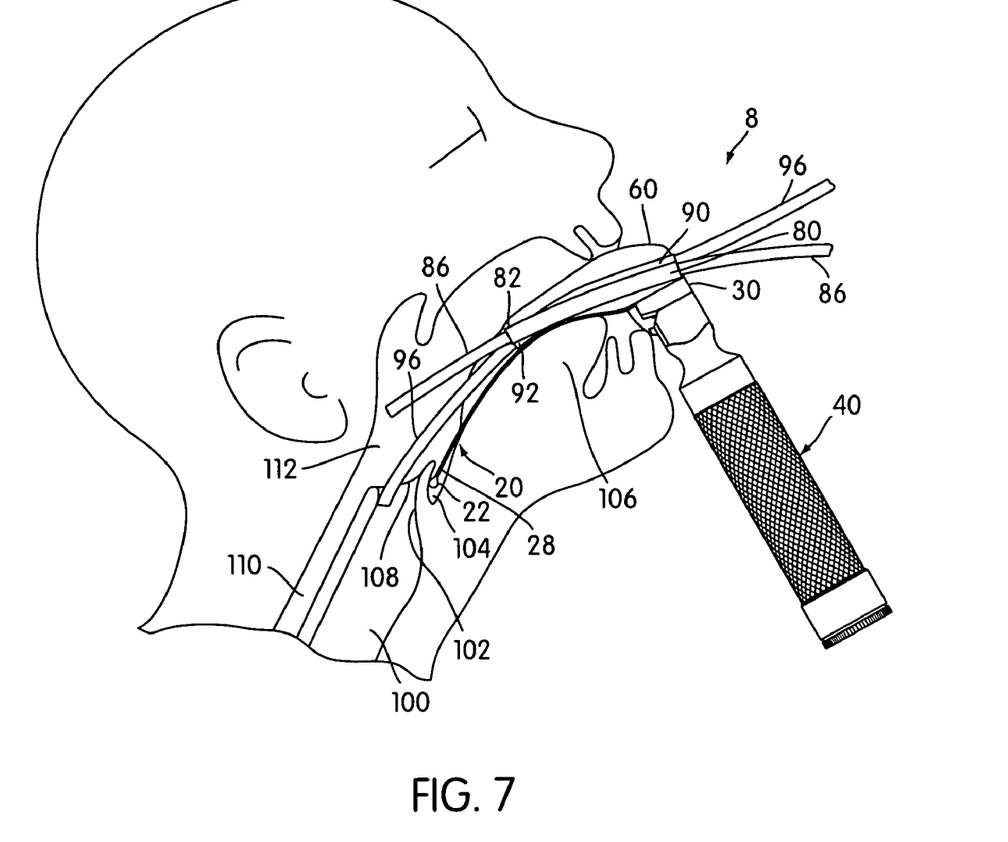
FIG. 7 is a side view illustrating the blade assembly when properly inserted in a patient to be intubated.

FIG. 7 illustrates blade assembly 10 when properly inserted in a patient to be intubated. As shown in FIG. 7, the blade assembly 10 is placed in the mouth of the patient with the curved blade 20 positioned atop the tongue 106 of the patient. The tip 22 at the distal and 28 is placed in the vallecula 104 between the tongue 106 and the epiglottis 102. Holding the handle 40 with one hand, a downward force is applied to the tongue 106, thereby causing the epiglottis 102 to curl up and over the tip 22 so as to expose the glottic aperture 108. With the glottic aperture 108 exposed, a tube can be inserted through the glottic aperture 108 and into the trachea 100.

As mentioned above, various secretions within the oral cavity can obscure view of the glottic aperture 108 and the trachea 100, and thus it becomes necessary to aspirate the secretions so as to achieve unobstructed observation of the glottic aperture 108 and trachea 100. Two locations at which aspiration is often necessary are at the glottic aperture 108 and at the laryngeal gutter 112 above the esophagus 110.

The present invention facilitates faster, more accurate aspiration of the glottic aperture 108 and laryngeal gutter 112 in that the first guide tube 80 and the second guide tube 90 are oriented so as to direct aspiration tubes to the laryngeal gutter 112 and the glottic aperture 108, respectively. More specifically, as shown in FIG. 7, first guide tube 80 is oriented on the blade 20 with an angle of attack such that a flexible tube 86 guided therethrough will be directed in the general direction of the laryngeal gutter 112. Similarly, the second guide tube 90 is oriented on the blade 20 with an angle of attack such that a flexible tube 96 guided therethrough will be directed in the general direction of the glottic aperture 108. Thus, aspiration tubes can be directed to each of these regions and to both regions simultaneously, if necessary, without requiring significant effort on the part of the operator to ensure that the tubes are properly directed to the desired location(s)

In an alternative embodiment, blade assembly 10 and handle 40 can be integrally connected at base 30. Additionally, blade assembly 10 can be constructed without light source 50 and/or tongue deflector 60 and horizontal flange 70.

Figure 8:
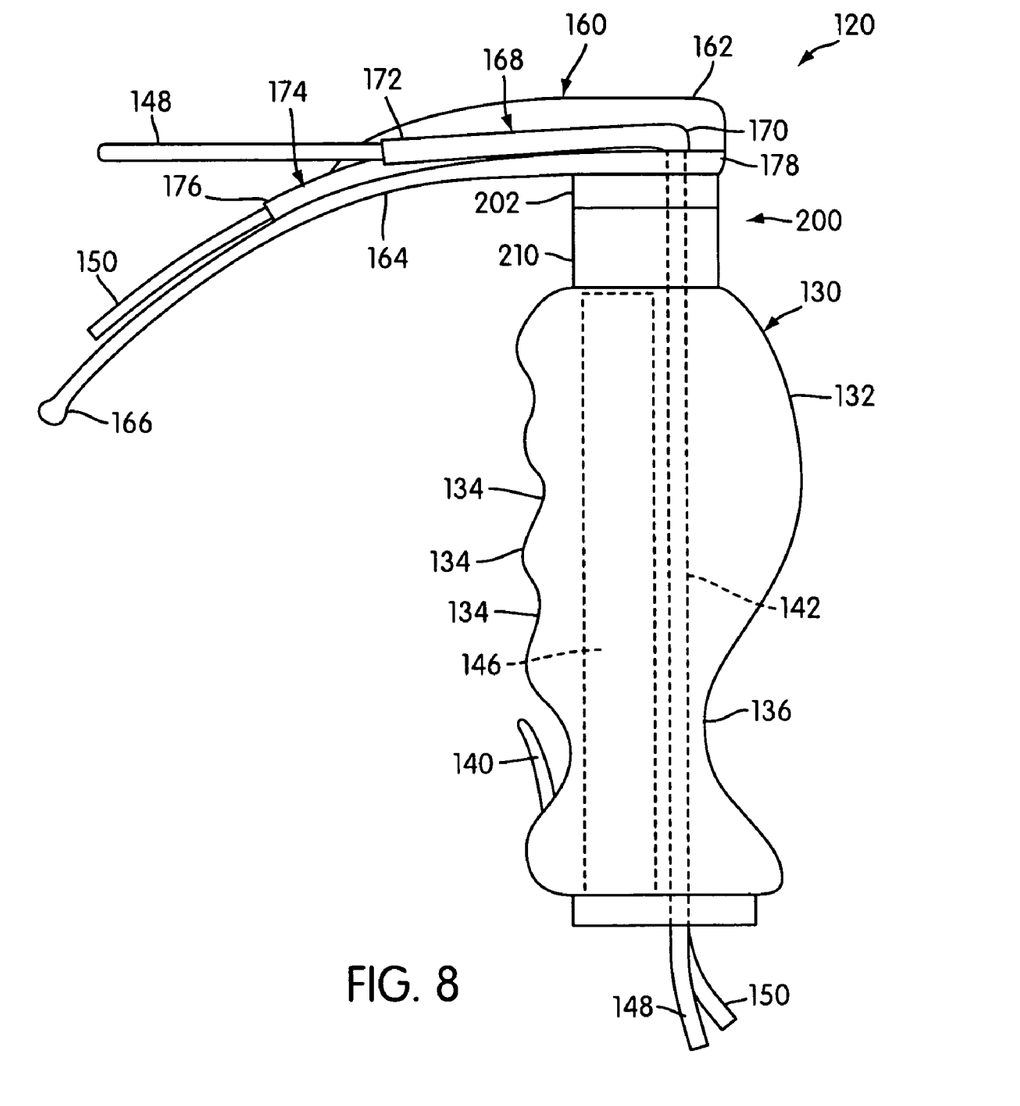
FIG. 8 is a side elevation of a laryngoscope according to further aspects of the present invention.

Other aspects of the invention are illustrated in FIGS. 8-12. As shown in FIG. 8, the laryngoscope 120 includes a handle 130 and a blade assembly 160 attached thereto. The blade assembly 160 is preferably connected to the handle 130 by a bayonette connection 200, described in more detail below. In accordance with another aspect of the invention, the handle 130 is provided with an ergonomic, hand-conforming shape to facilitate the application of the tongue-depressing force required to effect laryngeal suspension. More specifically, handle 130 includes on one side thereof a hump 132 to conform to the palm and heal of a hand grasping the handle 130 with the lower end of the grasping hand (i.e., the end, or side, of the hand opposite the thumb) closest to the blade. Handle 130 further includes finger contours 134 disposed on a side of the handle 130 generally opposite to the hump 132, and a narrowed portion 136 to conform to the web of the hand between the thumb and the index finger.

The blade assembly 160 includes a blade 164 (which is curved in the illustrated embodiment), having a proximal end 178 and a distal end 166, a tongue depressor 160, a first guide tube 168, and a second guide tube 174. The blade assembly 160 may also include a light, not shown.

As described above, and further shown in FIG. 10, when the laryngoscope is placed into the patient's oral cavity with the blade 164 positioned atop the tongue 106 and the distal end 166 positioned in the vallecula 104, laryngeal suspension is effected by applying a downward force, generally in the direction indicated by arrow V in an axial direction relative to a longitudinal axis of the handle 130. Applying the downward force in the direction V is facilitated with the ergonomic, hand-conforming handle 130 as compared to the cylindrically shaped handles of prior art laryngoscopes.

Although, laryngoscope 120 includes a curved blade, it will be appreciated by those having skill in the art that the benefits of the ergonomic, hand-conforming handle 130 can also be realized when used in conjunction with straight laryngoscope blades.

In a preferred embodiment, the laryngoscope of the present invention includes features that facilitate single-handed laryngeal suspension/aspiration/oxygenation. One or more triggers or other switches that are operable by the hand grasping the handle 130, such as trigger 140, are provided so that the user can, by operation of one of the triggers and/or switches, initiate and terminate aspiration and/or oxygenation. Aspiration is accomplished by extending a tube into the portion of the oral cavity to be aspirated and applying a vacuum to the tube. Similarly, oxygenation is accomplished by extending a tube into the trachea and then applying a flow of oxygen through the tube. In accordance with the present invention, it is contemplated that the extension of the appropriate tube(s) and the control of a vacuum and/or oxygen flow through the tube be effected by the operator manipulating one or more triggers and/or switches located on the handle 130.

Figure 9A:
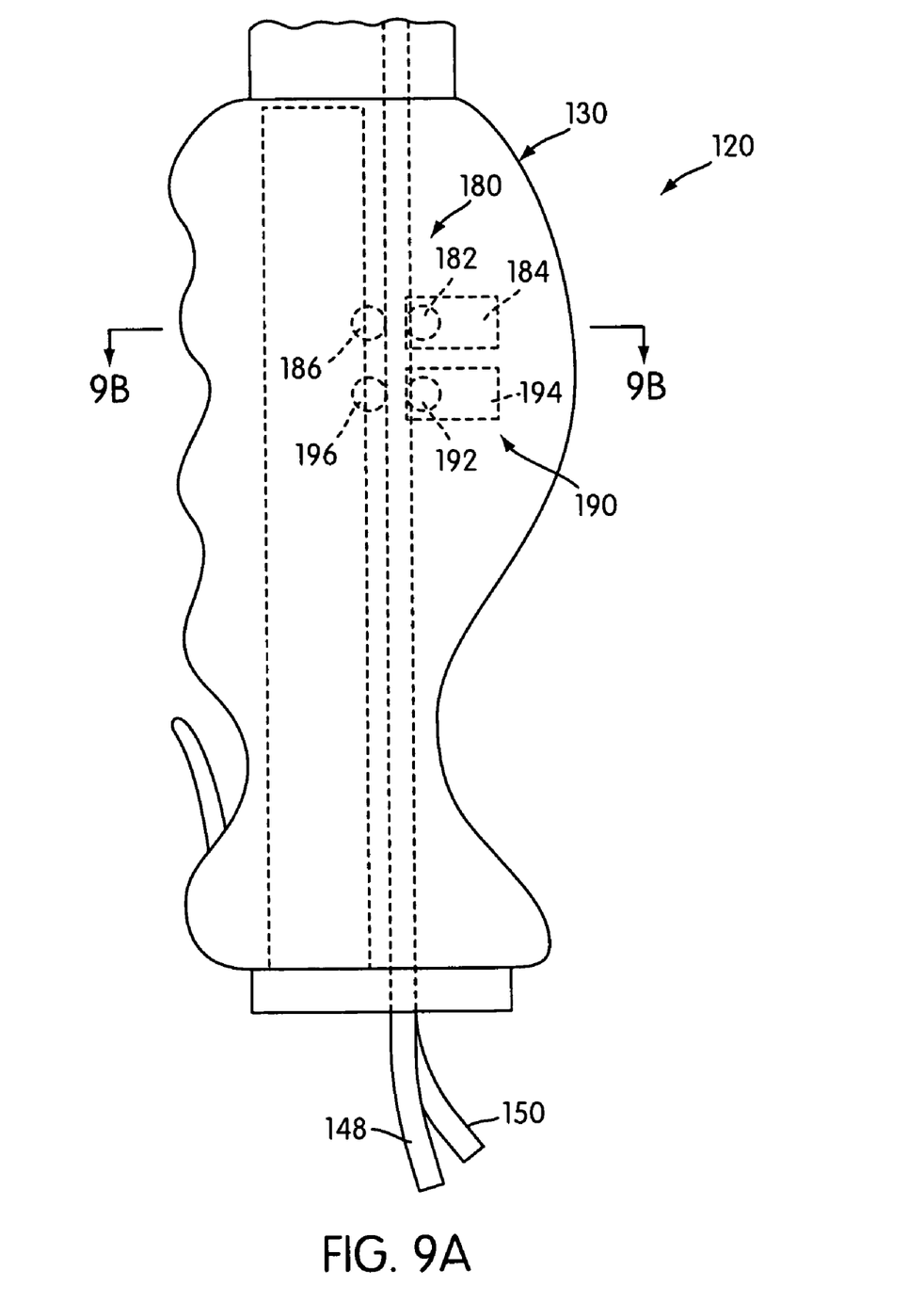
FIG. 9A is an enlarged partial side view of the handle of the laryngoscope of FIG. 8.
Figure 9B:
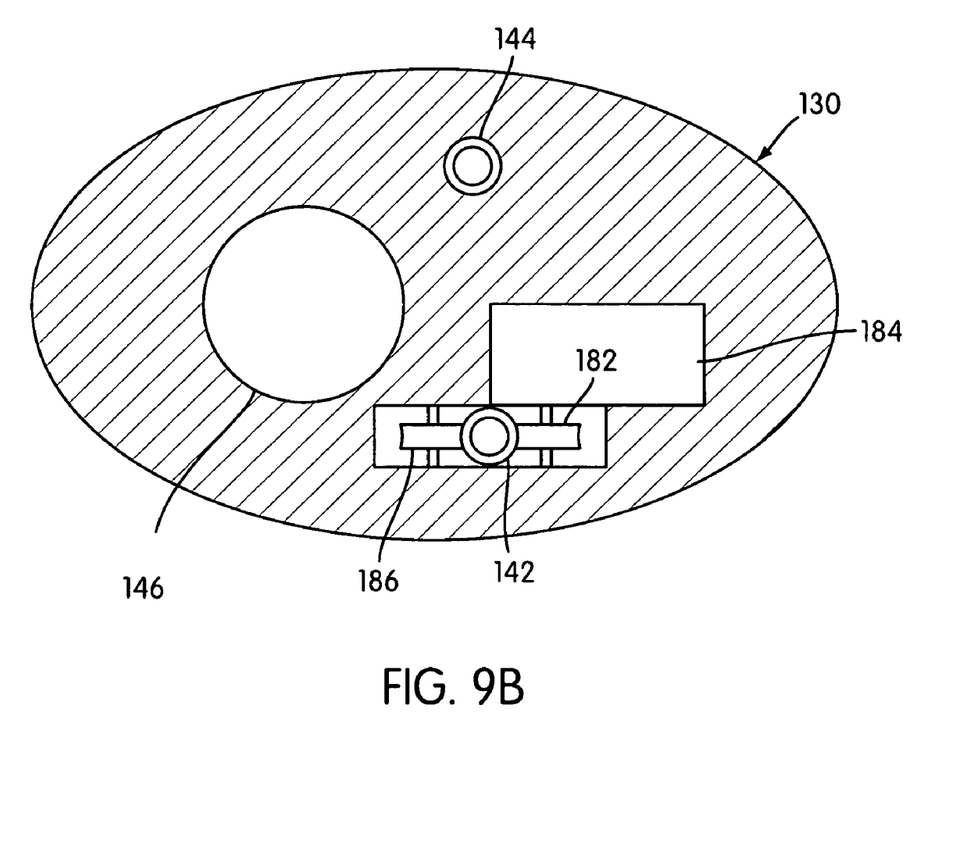
FIG. 9B is a cross section of the handle portion of the laryngoscope of FIG. 9A taken along the line 9B-9B.
Figure 10:
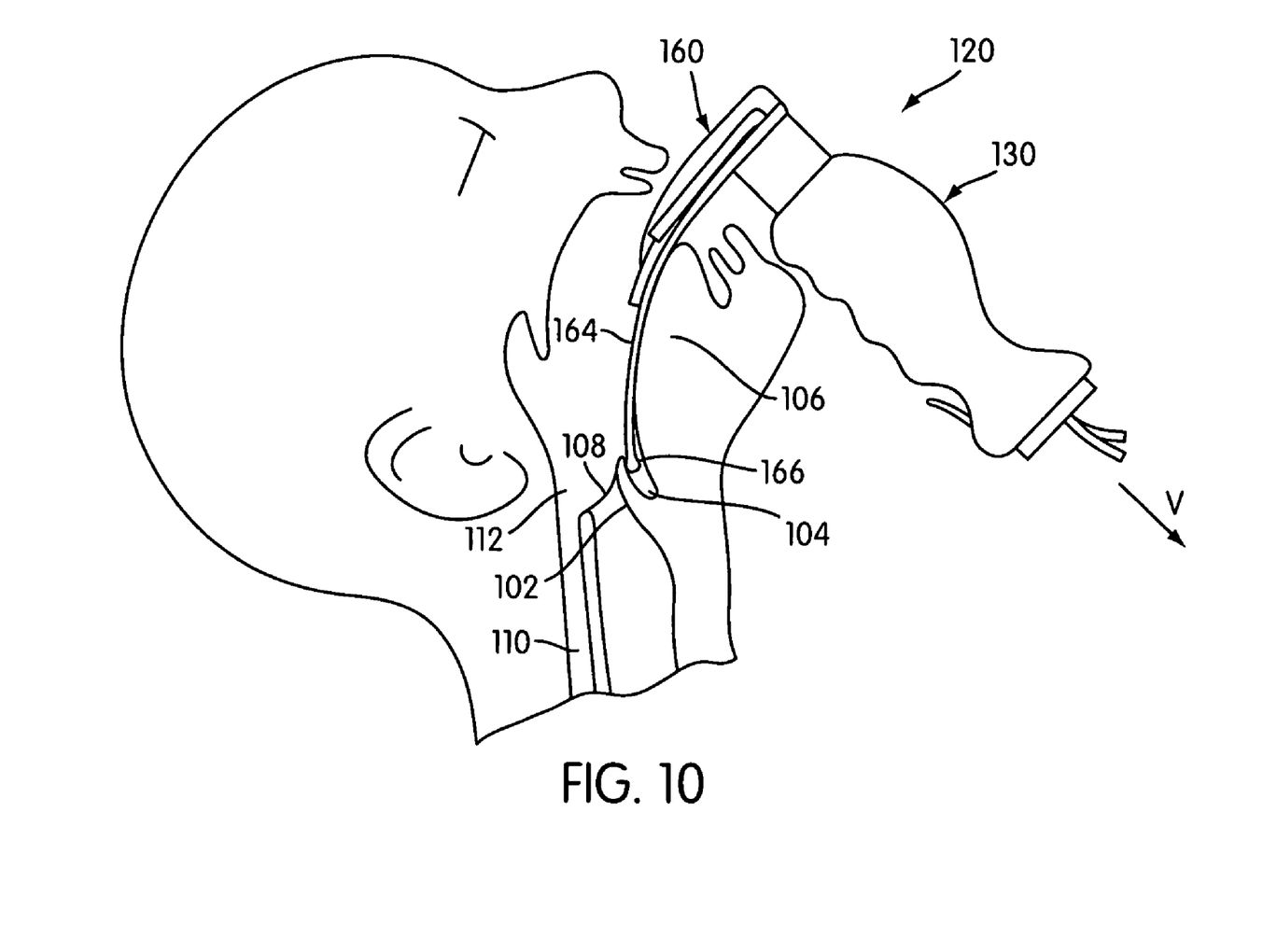
FIG. 10 is a side view illustrating the laryngoscope of FIG. 8 employed in a patient's mount and further illustrating a thrust vector to be applied with the laryngoscope to effect laryngeal suspension.

Accordingly, the laryngoscope of the present invention preferably includes one or more tube extension/retraction mechanisms constructed and arranged to permit the user grasping the handle of the laryngoscope to selectively effect extension of a tube into the oral cavity and retraction of the tube from the oral cavity by operation of a trigger or switch located on the handle. An example of such a mechanism is shown in FIGS. 9A and 9B. As shown, the handle 130 includes channels through which tubes 148, 150 may be directed. As shown in FIG. 8, the channels formed in the handle 130 direct the tubes 148, 150 through the handle 130 and into the first and second guide tubes 168, 174, respectively. The guide tubes 168, 174 each include a proximal elbow (only elbow 170 of first guide tube 168 is shown) to transition the tubes 148, 150 from the handle 130 into the guide tubes 168, 174, respectively. Each guide tube 168, 174 also includes a distal end 172, 176 from which the respective tube 148, 150 extends into the oral cavity.

The laryngoscope 120 includes tube extension/retraction mechanisms 180, 190 located in the handle 130 for effecting the powered extension and retraction of the tubes 148, 150. In the embodiment shown, tube extension/retraction mechanism 180 includes a drive wheel 182 drivingly coupled to a motor 184. The drive wheel 182 engages one side of the tube 148 while a guide wheel 186 engages an opposite side of the tube 148. Powered rotation of the drive wheel 182, as controlled by a switch such as trigger 140 located on the handle 130, causes corresponding extension or retraction of the tube 148, depending on the direction of rotation of the drive wheel 182. Tube extension/retraction mechanism 190 similarly includes a drive wheel 192 coupled to a motor 194 and a guide wheel 196 for causing powered extension and retraction of tube 150.

As an alternative, or in addition, to directing tubes 148, 150 through channels formed in the handle 130, it is also contemplated that one or more tubes could be directed, as is conventionally done manually, from behind the blade assembly 160 onto the proximal end 178 of the blade 164. A tube extension/retraction mechanism could be positioned on a bracket or other supporting structure (not shown) extending behind the proximal end 178 of the blade 164.

It is also contemplated that the laryngoscope could be constructed and arranged to provide for powered extension and retraction of only one tube or more than two tubes, with the size of the laryngoscope, the size of the tube(s), and the size of the extension/retraction mechanism(s) being the obvious factors limiting the maximum number of tubes that can be accommodated by the laryngoscope. In addition, the laryngoscope may include features which allow manual or powered extension and retraction of a tube.

In addition to providing powered extension and retraction of tubes, it is further contemplated that the laryngoscope 120 include functionality that allows the user to turn the vacuum and/or the oxygen flow on and off. Such functionality can be provided, for example, by including a valve mechanism in the handle 130 that controls suction and gas flow in the tubes, by including a clamping mechanism in the handle that pinches a tube to stop suction or gas flow, or by including a communication link (by wire or wireless) between the laryngoscope and the source of suction or gas flow. One or more switches or triggers can be provided on the handle for controlling the valve mechanism or clamping mechanism or for sending a signal to the source component.

The bayonette connection 200 provides an easy and secure connection between the handle 130 and the blade assembly 160 and also connects channels in the handle 130—through which the tubes 148 and 150 are passed—and the guide tubes 168 and 174. If a light is provided on the blade assembly, the bayonette connection will also provide an electrical connection between the light and the power source (e.g., batteries) carried in the handle 130.

The bayonette connection 200 includes a male part 202 and a female part 210. In the embodiment illustrated in FIGS. 11 and 12, the male part 202 is on the blade assembly 160 and the female part 210 is on the handle 130. Alternatively, the male part 202 and female part 210 can be interchanged and located on the handle 130 and blade assembly 160, respectively.

Figure 11:
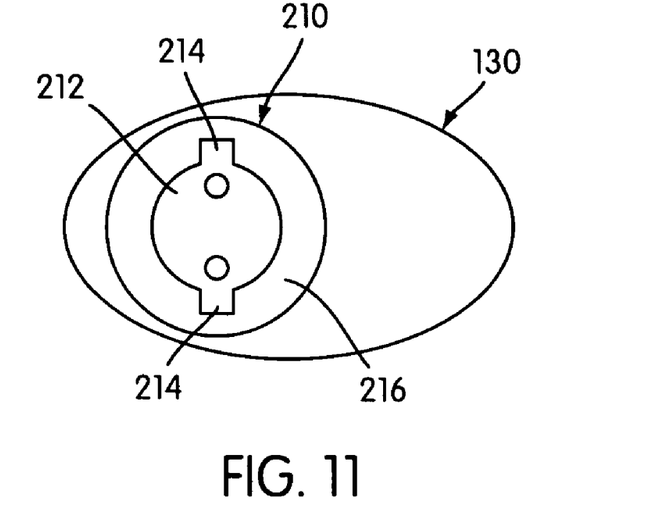
FIG. 11 is an end view of the handle of the laryngoscope showing a female portion of a bayonette connection for connecting the handle to a blade assembly.
Figure 12:
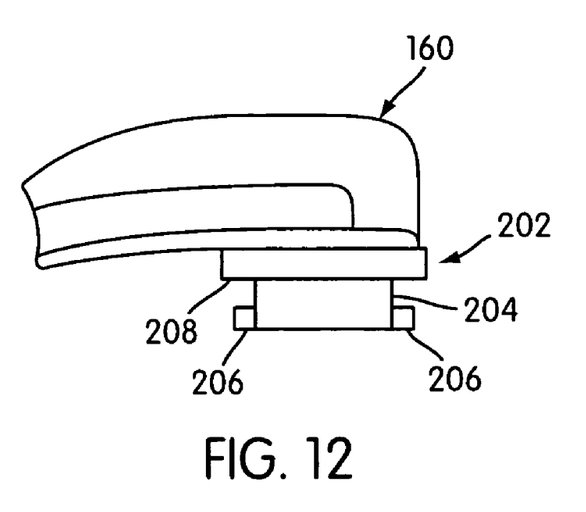
FIG. 12 is a side view of a male portion of the bayonette connection.

The male part 202 includes a cylindrical extension 204, radial tabs 206, and a collar 208. Female part 210 has a circular opening 212, radial slots 214, and collar 216. The male part 202 is connected to the female part 210 by aligning the radial tabs 206 with the radial slots 214 and inserting the cylindrical extension 204 into the circular opening 212. When the radial tabs 206 are aligned to the radial slots 214, the blade assembly 160 will be generally perpendicular to the handle 130. The cylindrical extension 204 is inserted into the circular opening 212 until the collar 208 of the male part 202 is in contact with the collar 216 of the female part 210. Then the blade assembly 160 is rotated 90 degrees with respect to the handle 130 to lock the blade assembly 160 and handle 130 together. The male part 202 and the female part 210 may include features, such as camming structures and/or detents for locking the blade assembly 160 and handle 130 in the proper operative positions.

The apparatus of the present invention thus provides the benefits of single-handed laryngeal suspension, secretion aspiration, oxygenation, and direct visualization. Additionally, the apparatus of the present invention allows a fibre-optic cable to be easily inserted into the trachea, which can be connected to a video device for purposes of indirect visualization. Such indirect visualization is useful for documentation, instruction, or to assist in tracheal intubation.

Finally, although a preferred embodiment is specifically illustrated and described herein, it will be appreciated that modifications and variations of the present invention are covered by the above teachings and within the purview of the appended claims without departing from the spirit and intended scope of this invention.

What is claimed is:

1. A blade assembly for a laryngoscope including a handle, said blade assembly comprising:
   base for coupling to the handle;
   an elongated blade secured to the base, said elongated blade having a proximal end, a distal end, an upper surface, and a lower surface, said lower surface of said elongated blade being secured to said base at said proximal end;
   a first guide tube affixed to said elongated blade and having a proximal end and a distal end; and
   a second guide tube affixed to said elongated blade adjacent said first guide tube and having a proximal end and a distal end, wherein
   said first and second guide tubes are constructed and arranged to direct tubes extended therethrough into the oral cavity of a patient;
   said first guide tube is substantially straight along its entire length and said second guide tube has a curved portion; and
   said elongated blade is curved, the curved portion of the second guide tube is curved in general conformity to the curvature of the elongated blade, and the first guide tube is not curved in general conformity to the curvature of the blade because said first guide tube is substantially straight along its entire length.

2. The blade assembly of claim 1, further comprising a light attached to said elongated blade.

3. The blade assembly of claim 1, further comprising a tongue deflector having a portion extending in a direction transverse to the upper surface of the elongated blade along a marginal edge segment of said elongated blade.

4. The blade assembly of claim 1, wherein said first and second guide tubes are oriented at different angles of attack with respect to said elongated blade so that when said elongated blade is placed atop the tongue of a patient to effect laryngeal suspension, said first and second guide tubes direct respective tubes extended therethrough into different regions of the patient's oral cavity.

5. The blade assembly of claim 1, wherein the proximal end of the first guide tube and the proximal end of the second guide tube are both positioned at the proximal end of the elongated blade.

6. The blade assembly of claim 5, wherein the distal end of the first guide tube and the distal end of the second guide tube are both positioned at about the midpoint of the elongated blade.

7. The blade assembly of claim 1, wherein the center of the distal end of the first guide tube is disposed above the center of the distal end of the second guide tube relative to the upper surface of the elongated blade.

8. The blade assembly of claim 7, wherein the center of the proximal end of the first guide tube is disposed below the center of the proximal end of the second guide tube relative to the upper surface of the elongated blade.

9. The blade assembly of claim 1, further comprising a first aspiration tube inserted into the first guide tube and a second aspiration tube inserted into the second guide tube.

10. The blade assembly of claim 1, wherein said blade does not have an opening at its distal end.

11. The blade assembly of claim 1, wherein said blade is not hollow.

12. The blade assembly of claim 1, wherein said blade is not in the form of a tube.

13. An assembly, comprising:
    a base;
    an elongated blade secured to the base, said elongated blade having a proximal end, a distal end, an upper surface, and a lower surface, said lower surface of said elongated blade being secured to said base at said proximal end;
    a first guide means for guiding a first aspiration tube to a patient's laryngeal gutter, said first guide means being affixed to said elongated blade; and
    a second guide means for guiding a second aspiration tube to a patient's glottic aperture, said second guide means being affixed to said elongated blade, wherein
    said first guide means is substantially straight along its entire length and said second guide means has a curved portion; and
    said elongated blade is curved, the curved portion of the second guide means is curved in general conformity to the curvature of the elongated blade, and the first guide means is not curved in general conformity to the curvature of the blade because said first guide means is substantially straight along its entire length.

14. The assembly of claim 13, wherein said first guide means comprises a first guide tube having a proximal end and a distal end and said second guide means comprises a second guide tube having a proximal end and a distal end.

15. The assembly of claim 14, wherein the proximal end of the first guide tube and the proximal end of the second guide tube are both positioned at the proximal end of the elongated blade.

16. The assembly of claim 15, wherein the distal end of the first guide tube and the distal end of the second guide tube are both positioned at about the midpoint of the elongated blade.

17. The assembly of claim 14, wherein the center of the distal end of the first guide tube is disposed above the center of the distal end of the second guide tube relative to the upper surface of the elongated blade, and wherein the center of the proximal end of the first guide tube is disposed below the center of the proximal end of the second guide tube relative to the upper surface of the elongated blade.

18. The assembly of claim 14, further comprising a first aspiration tube inserted into the first guide tube and a second aspiration tube inserted into the second guide tube.

19. The assembly of claim 14, wherein said first and second guide tubes are oriented at different angles of attack with respect to said elongated blade.

20. The assembly of claim 14, wherein said first guide tube is substantially straight and said second guide tube has a curved portion.

21. The assembly of claim 20, wherein said elongated blade is curved and said curved portion of the second guide tube follows the curve of the elongated blade.

* * * * *

UNITED STATES PATENT AND TRADEMARK OFFICE
CERTIFICATE OF CORRECTION

PATENT NO. : 7,608,040 B1  Page 1 of 1
APPLICATION NO. : 10/783093
DATED : October 27, 2009
INVENTOR(S) : Mordecai Dunst It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 237 days.

Signed and Sealed this

Twelfth Day of October, 2010

David J. Kappos
*Director of the United States Patent and Trademark Office*